(12) United States Patent
Merritt et al.

(10) Patent No.: US 10,881,413 B2
(45) Date of Patent: Jan. 5, 2021

(54) SYSTEMS AND METHODS FOR EMBOLIZATION OF BODY STRUCTURES

(71) Applicant: Sequent Medical, Inc., Aliso Viejo, CA (US)

(72) Inventors: Brian E. Merritt, San Clemente, CA (US); Todd J. Hewitt, Laguna Niguel, CA (US)

(73) Assignee: Sequent Medical, Inc., Aliso Viejo, CA (US)

( * ) Notice: Subject to any disclaimer, the term of this patent is extended or adjusted under 35 U.S.C. 154(b) by 321 days.

(21) Appl. No.: 15/923,266

(22) Filed: Mar. 16, 2018

(65) Prior Publication Data

US 2018/0271540 A1    Sep. 27, 2018

Related U.S. Application Data

(60) Provisional application No. 62/476,104, filed on Mar. 24, 2017.

(51) Int. Cl.
| | | |
|---|---|---|
| *A61B 17/12* | (2006.01) | |
| *A61B 17/00* | (2006.01) | |
| *A61B 90/00* | (2016.01) | |

(52) U.S. Cl.
CPC .. *A61B 17/12172* (2013.01); *A61B 17/12113* (2013.01); *A61B 2017/00867* (2013.01); *A61B 2017/1205* (2013.01); *A61B 2017/12054* (2013.01); *A61B 2090/3966* (2016.02)

(58) Field of Classification Search
CPC .......... A61B 17/0057; A61B 17/12022; A61B 17/12113; A61B 17/1214; A61B 17/12145; A61B 17/12168; A61B 17/12172; A61B 17/12177; A61B 2017/00575; A61B 2017/00592; A61B 2017/00597; A61B 2017/00606
See application file for complete search history.

(56) References Cited

U.S. PATENT DOCUMENTS

| | | | | |
|---|---|---|---|---|
| 6,368,338 | B1 * | 4/2002 | Konya | ............. A61B 17/12022 606/200 |
| 2011/0213403 | A1 | 9/2011 | Aboytes | |
| 2012/0271337 | A1 | 10/2012 | Figulla et al. | |

(Continued)

OTHER PUBLICATIONS

WIPO, U.S. International Search Authority, International Search Report and Written Opinion dated May 24, 2018 in International Patent Application No. PCT/US2018/022806, 9 pages.

*Primary Examiner* — Robert A Lynch
(74) *Attorney, Agent, or Firm* — Inskeep IP Group, Inc.

(57) ABSTRACT

A device for treatment of a vascular defect within a patient's vasculature includes a self-expanding permeable shell having a proximal end, a distal end, and a longitudinal axis, the shell comprising a plurality of elongate resilient filaments having a braided structure, wherein the filaments are secured at at least one of the proximal end or the distal end of the permeable shell, wherein the permeable shell has a radially constrained elongated state configured for delivery within a microcatheter and has an expanded state with an axially shortened configuration relative to the radially constrained state, the permeable shell having a plurality of openings formed between the braided filaments, wherein the permeable shell in its expanded state comprises a plurality of circumferentially-arrayed lobes.

16 Claims, 5 Drawing Sheets

(56) References Cited

U.S. PATENT DOCUMENTS

2014/0358178 A1* 12/2014 Hewitt ............. A61B 17/12113
                                                              606/200
2015/0066077 A1      3/2015 Akpinar
2015/0351731 A1* 12/2015 Brown ............... A61B 17/0057
                                                              600/16

* cited by examiner

SYSTEMS AND METHODS FOR EMBOLIZATION OF BODY STRUCTURES

RELATED APPLICATIONS

This application claims benefit of and priority to U.S. Provisional Application Ser. No. 62/476,104 filed Mar. 24, 2017 entitled Systems And Methods For Embolization Of Body Structures, which is hereby incorporated herein by reference in its entirety.

FIELD OF THE INVENTION

Embodiments of devices and methods herein are directed to blocking a flow of fluid through a tubular vessel or into a small interior chamber of a saccular cavity or vascular defect within a mammalian body. More specifically, embodiments herein are directed to devices and methods for treatment of a vascular defect of a patient including some embodiments directed specifically to the treatment of cerebral aneurysms of patients.

BACKGROUND

The mammalian circulatory system is comprised of a heart, which acts as a pump, and a system of blood vessels that transport the blood to various points in the body. Due to the force exerted by the flowing blood on the blood vessel the blood vessels may develop a variety of vascular defects. One common vascular defect known as an aneurysm results from the abnormal widening of the blood vessel. Typically, vascular aneurysms are formed as a result of the weakening of the wall of a blood vessel and subsequent ballooning and expansion of the vessel wall. If, for example, an aneurysm is present within an artery of the brain, and the aneurysm should burst with resulting cranial hemorrhaging, death could occur.

Surgical techniques for the treatment of cerebral aneurysms typically involve a craniotomy requiring creation of an opening in the skull of the patient through which the surgeon can insert instruments to operate directly on the patient's brain. For some surgical approaches, the brain must be retracted to expose the parent blood vessel from which the aneurysm arises. Once access to the aneurysm is gained, the surgeon places a clip across the neck of the aneurysm thereby preventing arterial blood from entering the aneurysm. Upon correct placement of the clip the aneurysm will be obliterated in a matter of minutes. Surgical techniques may be effective treatment for many aneurysms. Unfortunately, surgical techniques for treating these types of conditions include major invasive surgical procedures that often require extended periods of time under anesthesia involving high risk to the patient. Such procedures thus require that the patient be in generally good physical condition in order to be a candidate for such procedures.

Various alternative and less invasive procedures have been used to treat cerebral aneurysms without resorting to major surgery. Some such procedures involve the delivery of embolic or filling materials into an aneurysm. The delivery of such vaso-occlusion devices or materials may be used to promote hemostasis or fill an aneurysm cavity entirely. Vaso-occlusion devices may be placed within the vasculature of the human body, typically via a catheter, either to block the flow of blood through a vessel with an aneurysm through the formation of an embolus or to form such an embolus within an aneurysm stemming from the vessel. A variety of implantable, coil-type vaso-occlusion devices are known. The coils of such devices may themselves be formed into a secondary coil shape, or any of a variety of more complex secondary shapes. Vaso-occlusive coils are commonly used to treat cerebral aneurysms but suffer from several limitations including poor packing density, compaction due to hydrodynamic pressure from blood flow, poor stability in wide-necked aneurysms and complexity and difficulty in the deployment thereof as most aneurysm treatments with this approach require the deployment of multiple coils.

Another approach to treating aneurysms without the need for invasive surgery involves the placement of sleeves or stents into the vessel and across the region where the aneurysm occurs. Such devices maintain blood flow through the vessel while reducing blood pressure applied to the interior of the aneurysm. Certain types of stents are expanded to the proper size by inflating a balloon catheter, referred to as balloon expandable stents, while other stents are designed to elastically expand in a self-expanding manner. Some stents are covered typically with a sleeve of polymeric material called a graft to form a stent-graft. Stents and stent-grafts are generally delivered to a preselected position adjacent a vascular defect through a delivery catheter. In the treatment of cerebral aneurysms, covered stents or stent-grafts have seen very limited use due to the likelihood of inadvertent occlusion of small perforator vessels that may be near the vascular defect being treated.

In addition, current uncovered stents are generally not sufficient as a stand-alone treatment. In order for stents to fit through the microcatheters used in small cerebral blood vessels, their density is usually reduced such that when expanded there is only a small amount of stent structure bridging the aneurysm neck. Thus, they do not block enough flow to cause clotting of the blood in the aneurysm and are thus generally used in combination with vaso-occlusive devices, such as the coils discussed above, to achieve aneurysm occlusion.

A number of aneurysm neck bridging devices with defect spanning portions or regions have been attempted; however, none of these devices has had a significant measure of clinical success or usage. A major limitation in their adoption and clinical usefulness is the inability to position the defect spanning portion to assure coverage of the neck. Existing stent delivery systems that are neurovascular compatible (i.e., deliverable through a microcatheter and highly flexible) do not have the necessary rotational positioning capability. Another limitation of many aneurysm bridging devices described in the prior art is the poor flexibility. Cerebral blood vessels are tortuous and a high degree of flexibility is required for effective delivery to most aneurysm locations in the brain.

Recently, devices and methods have been developed for delivery and use in small and tortuous blood vessels that can substantially block the flow of blood into an aneurysm, such as a cerebral aneurysm. In some cases, these devices achieve short term results, but may be prone to compression or other changes in shape or orientation, which may result in recanalization of the aneurysm. New methods and devices are desired which are suitable for blocking blood flow in cerebral aneurysms over an extended period of time without a significant risk of deformation, compaction or dislocation.

SUMMARY OF THE INVENTION

In an embodiment of the present disclosure, a device for treatment of a vascular defect within a patient's vasculature includes a self-expanding permeable shell having a proximal end, a distal end, and a longitudinal axis, the shell comprising a plurality of elongate resilient filaments having a braided structure, wherein the filaments are secured at at least one of the proximal end or the distal end of the permeable shell, wherein the permeable shell has a radially constrained elongated state configured for delivery within a microcatheter and has an expanded state with an axially shortened configuration relative to the radially constrained state, the permeable shell having a plurality of openings formed between the braided filaments, wherein the permeable shell in its expanded state comprises a plurality of circumferentially-arrayed lobes.

In another embodiment of the present disclosure, a device for treatment of a vascular defect within a patient's vasculature includes a self-expanding permeable shell having a proximal end, a distal end, and a longitudinal axis, the shell comprising a plurality of elongate resilient filaments having a braided structure, wherein the filaments are secured at at least one of the proximal end or the distal end of the permeable shell, wherein the permeable shell has a radially constrained elongated state configured for delivery within a microcatheter and has an expanded state with an axially shortened configuration relative to the radially constrained state, the permeable shell having a plurality of openings formed between the braided filaments, wherein the permeable shell in its expanded state comprises at least one recess extending circumferentially around at least a portion of a perimeter of the permeable shell.

DETAILED DESCRIPTION

Figure 1:
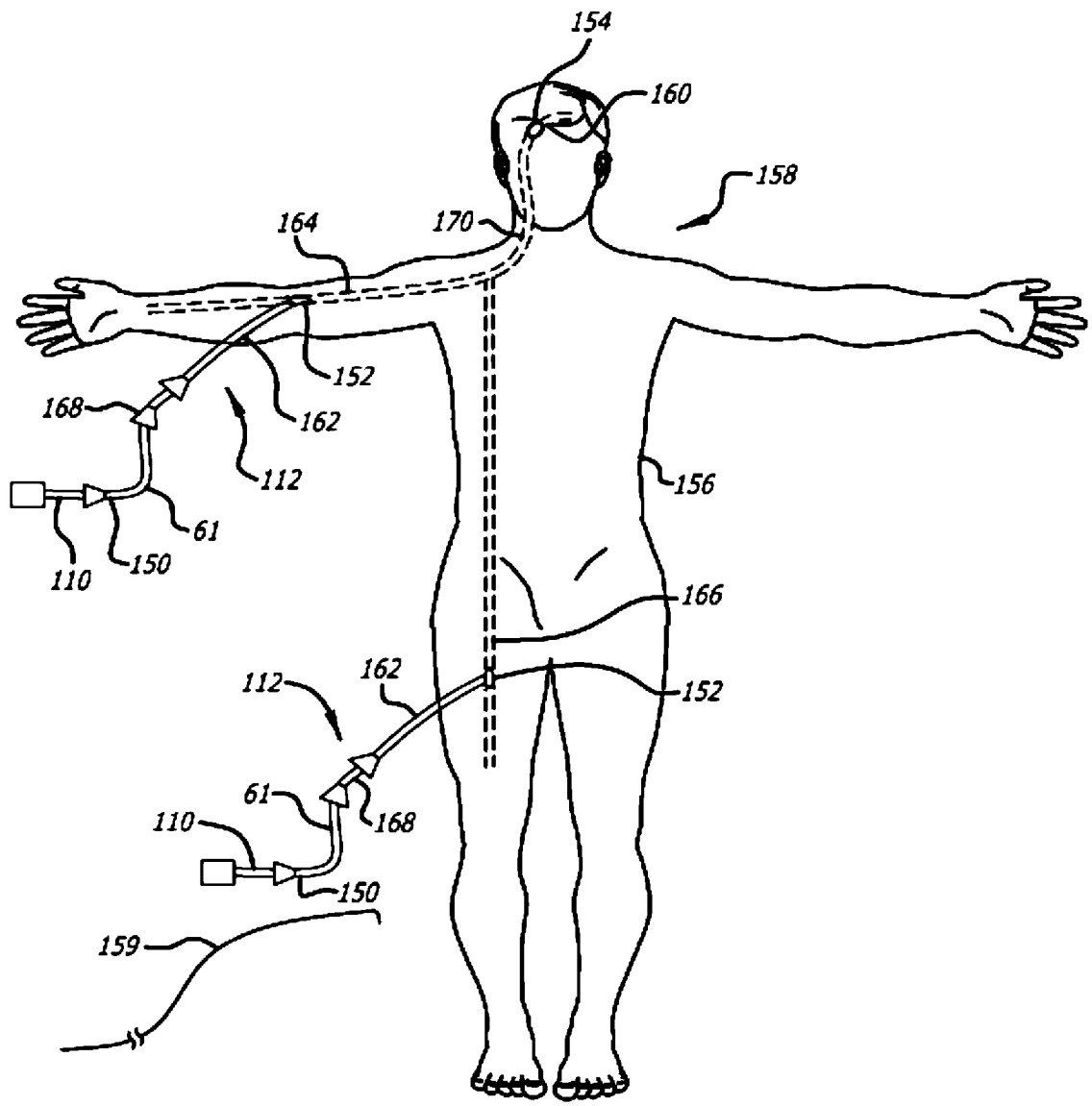
FIG. 1 is a schematic view of a patient being accessed by an introducer sheath, a microcatheter and a device for treatment of a patient's vasculature releasably secured to a distal end of a delivery device or actuator.

Discussed herein are devices and methods for the treatment of vascular defects that are suitable for minimally invasive deployment within a patient's vasculature, and particularly, within the cerebral vasculature of a patient. For such embodiments to be safely and effectively delivered to a desired treatment site and effectively deployed, some device embodiments may be configured for collapse to a low profile constrained state with a transverse dimension suitable for delivery through an inner lumen of a microcatheter and deployment from a distal end thereof. Embodiments of these devices may also maintain a clinically effective configuration with sufficient mechanical integrity once deployed so as to withstand dynamic forces within a patient's vasculature over time that may otherwise result in compaction of a deployed device. Unless otherwise stated, one or more of the features, dimensions, or materials of the various embodiments may be used in other similar embodiments discussed herein.

Some embodiments are particularly useful for the treatment of cerebral aneurysms by reconstructing a vascular wall so as to wholly or partially isolate a vascular defect from a patient's blood flow. Some embodiments may be configured to be deployed within a vascular defect to facilitate reconstruction, bridging of a vessel wall or both in order to treat the vascular defect. For some of these embodiments, a permeable shell of the device may be configured to anchor or fix the permeable shell in a clinically beneficial position. For some embodiments, the device may be disposed in whole or in part within the vascular defect in order to anchor or fix the device with respect to the vascular structure or defect. The permeable shell may be configured to span an opening, neck or other portion of a vascular defect in order to isolate the vascular defect, or a portion thereof, from the patient's nominal vascular system in order allow the defect to heal or to otherwise minimize the risk of the defect to the patient's health.

For some or all of the embodiments of devices for treatment of a patient's vasculature discussed herein, the permeable shell may be configured to allow some initial perfusion of blood through the permeable shell. The porosity of the permeable shell may be configured to sufficiently isolate the vascular defect so as to promote healing and isolation of the defect, but allow sufficient initial flow through the permeable shell so as to reduce or otherwise minimize the mechanical force exerted on the membrane the dynamic flow of blood or other fluids within the vasculature against the device. For some embodiments of devices for treatment of a patient's vasculature, only a portion of the permeable shell that spans the opening or neck of the vascular defect, sometimes referred to as a defect spanning portion, need be permeable and/or conducive to thrombus formation in a patient's bloodstream. For such embodiments, that portion of the device that does not span an opening or neck of the vascular defect may be substantially non-permeable or completely permeable with a pore or opening configuration that is too large to effectively promote thrombus formation.

In general, it may be desirable in some cases to use a hollow, thin walled device with a permeable shell of resilient material that may be constrained to a low profile for delivery within a patient. Such a device may also be configured to expand radially outward upon removal of the constraint such that the shell of the device assumes a larger volume and fills or otherwise occludes a vascular defect within which it is deployed. The outward radial expansion of the shell may serve to engage some or all of an inner surface of the vascular defect whereby mechanical friction between an outer surface of the permeable shell of the device and the inside surface of the vascular defect effectively anchors the device within the vascular defect. Some embodiments of such a device may also be partially or wholly mechanically captured within a cavity of a vascular defect, particularly where the defect has a narrow neck portion with a larger interior volume. In order to achieve a low profile and volume for delivery and be capable of a high ratio of expansion by volume, some device embodiments include a matrix of woven or braided filaments that are coupled together by the interwoven structure so as to form a self-expanding permeable shell having a pore or opening pattern between couplings or intersections of the filaments that is substantially regularly spaced and stable, while still allowing for conformity and volumetric constraint.

As used herein, the terms woven and braided are used interchangeably to mean any form of interlacing of filaments to form a mesh structure. In the textile and other industries, these terms may have different or more specific meanings depending on the product or application such as whether an article is made in a sheet or cylindrical form. For purposes of the present disclosure, these terms are used interchangeably.

Some embodiments for devices and methods for the treatment of vascular defects having permeable shells are described in U.S. Pat. No. 9,078,658, issued Jul. 14, 2015, and titled "Filamentary Devices for Treatment of Vascular Defects," which is incorporated herein by reference in its entirety for all purposes. Further embodiments for devices and methods for the treatment of vascular defects having permeable shells are described in co-owned U.S. Patent Application Publication No. 2016/02409934, published Sep. 1, 2016, and titled "Filamentary Devices for Treatment of Vascular Defects," which is incorporated herein by reference in its entirety for all purposes.

Embodiments for devices and methods for forming tubular braids to for creating permeable shells such as those described herein are described in U.S. Pat. No. 9,528,205, issued Dec. 27, 2016, and titled "Braiding Mechanism and Methods of Use," which is incorporated herein by reference in its entirety for all purposes. Devices for the treatment of vascular defects having permeable shells may be attached to delivery devices and delivered to vascular defects using embodiments of devices and methods such as those described in U.S. Pat. No. 8,876,855, issued Nov. 4, 2014, and titled "Delivery and Detachment Systems and Methods for Vascular Implants," which is incorporated herein by reference in its entirety for all purposes.

Embodiments of a delivery apparatus 110 may generally have a length greater than the overall length of a microcatheter 61 to be used for a delivery system 112. This relationship allows the delivery apparatus 110 to extend, along with an implantable device secured to the distal end thereof, from the distal port of the inner lumen 111 of the microcatheter 61 (FIG. 3) while having sufficient length extending from a proximal end 150 of the microcatheter 61, shown in FIG. 1, to enable manipulation thereof by a physician. For some embodiments, the length of the delivery apparatus 110 may be about 170 cm to about 200 cm. A patient 158 is shown in FIG. 1 undergoing treatment of a vascular defect 160, which may be a cerebral aneurysm. An access sheath 162 is shown disposed within either a radial artery 164 or femoral artery 166 of the body 156 of the patient 158 with the delivery system 112 that includes a microcatheter 61 and delivery apparatus 110 disposed within the access sheath 162. The delivery system 112 is shown extending distally into the vasculature of the patient's brain adjacent a vascular defect 160 in the patient's brain.

Access to a variety of blood vessels of a patient may be established, including arteries such as the femoral artery 166, radial artery 164, or other blood vessels, in order to achieve percutaneous access to a vascular defect 160. In general, the access artery may be exposed via a small surgical incision 152 and access to the lumen of the blood vessel is gained using the Seldinger technique where an introducing needle is used to place a wire over which a dilator or series of dilators dilates a vessel allowing an introducer sheath 162 to be inserted into the vessel. This would allow the device to be used percutaneously. With an introducer sheath 162 in place, a guiding catheter 168 is then used to provide a safe passageway from the entry site to a region near the target site 154 to be treated. For example, in treating a site in the human brain, a guiding catheter 168 would be chosen which would extend from the entry site 152 at the femoral artery up through the large arteries extending around the heart through the aortic arch, and downstream through one of the arteries extending from the upper side of the aorta such as the carotid artery 170. Typically, a guidewire 159 and microcatheter 61 are then placed through the guiding catheter 168 and advanced through the patient's vasculature, until a distal end of the microcatheter 61 is disposed adjacent or within the target vascular defect 160, such as an aneurysm.

Figure 2:
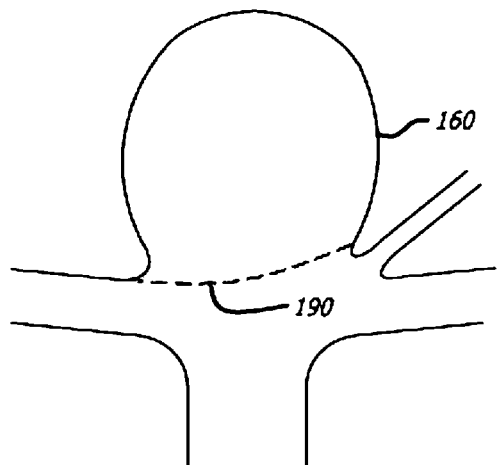
FIG. 2 shows a deployment sequence of a device for treatment of a patient's vasculature.
Figure 3:
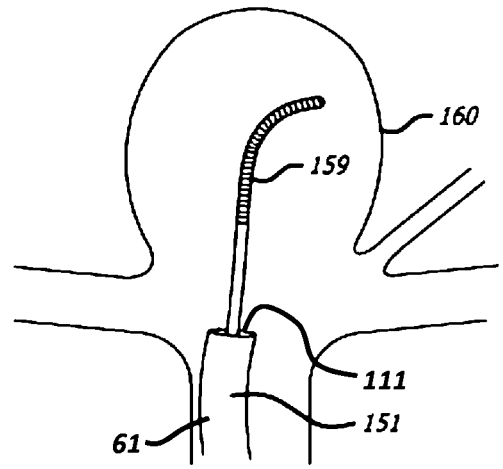
FIG. 3 shows a deployment sequence of a device for treatment of a patient's vasculature.

Once a properly sized device 10 (FIGS. 2-5) has been selected, the delivery and deployment process may then proceed. It should also be noted also that the properties of the device embodiments 10 and delivery system embodiments 112 discussed herein generally allow for retraction of a device 10 after initial deployment into a defect 160, but before detachment of the device 10. Therefore, it may also be possible and desirable to withdraw or retrieve an initially deployed device 10 after the fit within the defect 160 has been evaluated in favor of a differently sized device 10. An example of a terminal aneurysm 160 is shown in FIG. 2 in section. The tip 151 of a catheter, such as a microcatheter 61 may be advanced into or adjacent the vascular site or defect 160 (e.g., aneurysm) as shown in FIG. 3. For some embodiments, an embolic coil or other vaso-occlusive device or material may optionally be placed within the aneurysm 160 to provide a framework for receiving the device 10. In addition, a stent may be placed within a parent vessel of some aneurysms substantially crossing the aneurysm neck prior to or during delivery of devices for treatment of a patient's vasculature discussed herein.

Figure 4:
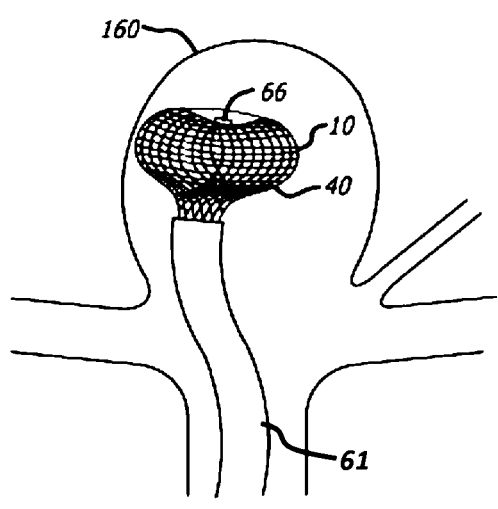
FIG. 4 shows a deployment sequence of a device for treatment of a patient's vasculature.

Detachment of the device 10 from the delivery apparatus 110 may be controlled by a control switch disposed at a proximal end of the delivery system 112 (FIG. 1), which may also be coupled to an energy source, which severs a tether 72 that secures the device 10 to the delivery apparatus 110. Once the device 10 is pushed out of the distal port of the microcatheter 61, or the radial constraint is otherwise removed, a distal end 66 of the device 10 may then axially move towards a proximal end 67 so as to assume the globular everted configuration within the vascular defect 160 as shown in FIGS. 4-5.

The device 10 may be inserted through the microcatheter 61 such that the catheter lumen 111 restrains radial expansion of the device 10 during delivery. Once the distal tip or deployment port of the delivery system 112 is positioned in a desirable location adjacent or within a vascular defect 160, the device 10 may be deployed out the distal end of the catheter 61 thus allowing the device to begin to radially expand as shown in FIG. 4. As the device 10 emerges from the distal end of the delivery system 112, the device 10 expands to an expanded state within the vascular defect 160, as shown in FIG. 5, but may be at least partially constrained by an interior surface of the vascular defect 160.

Figure 5:
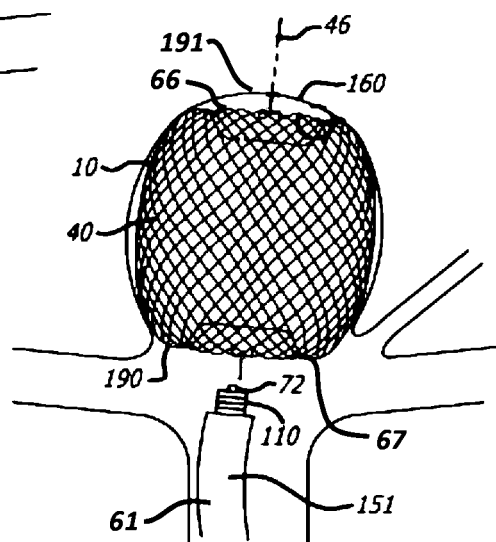
FIG. 5 shows a deployment sequence of a device for treatment of a patient's vasculature.

Upon complete deployment, radial expansion of the device 10 may serve to secure the device 10 within the vascular defect 160 and also deploy the permeable shell 40 across at least a portion of an opening 190 (e.g., aneurysm neck) so as to at least partially isolate the vascular defect 160 from flow, pressure or both of the patient's vasculature adjacent the vascular defect 160 as shown in FIG. 5. The conformability of the device 10, particularly in the neck region 190 may provide for improved sealing. For some embodiments, once deployed, the permeable shell 40 may substantially slow flow of fluids, impede flow into the vascular site, and thus reduce pressure within the vascular defect 160. For some embodiments, the device 10 may be implanted substantially within the vascular defect 160, however, in some embodiments, a portion of the device 10 may extend into the defect opening or neck 190 or into branch vessels. The longitudinal axis 46 of the permeable shell 40 is shown in FIG. 5 extending along a maximum projection of the vascular defect 160 (e.g., from the neck 190 to the dome 191). In other cases, the device 10 may be placed so that the permeable shell 40 has a different orientation in regard to the vascular defect 160, such that the longitudinal axis 46 of the permeable shell extends transversely or obliquely in relation to the neck 190 and dome 191.

Figure 6:
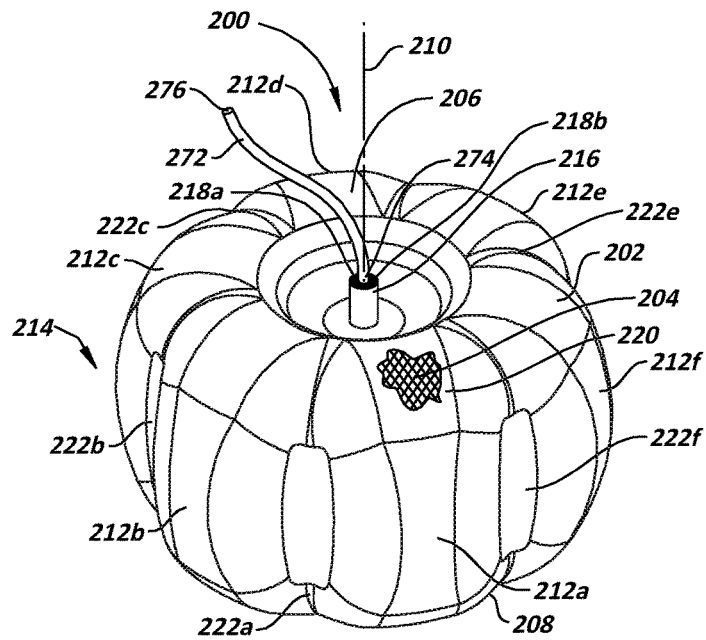
FIG. 6 is a perspective view of a device for treatment of vascular deformities according to an embodiment of the present disclosure.

FIG. 6 illustrates device for treatment of a vascular defect 200 comprising a permeable shell 202 which is woven or braided from a plurality of resilient elongate filaments 204. The resilient elongate filaments 204 are only partially shown to simplify the depiction, but in actuality make up generally the entire structure of the permeable shell 202. The permeable shell 202 has a first end 206, a second end 208, and a longitudinal axis 210. In some embodiments, the elongate resilient filaments 204 of the permeable shell 202 may have a transverse cross section that is substantially round in shape and be made from a superelastic material that may also be a shape memory metal. The filaments 204 are bonded, welded, or otherwise secured together at the first end 206. In the embodiment of FIG. 6, a collar 216 is fastened around ends 218 of the filaments 204, by crimping, welding, adhesive or epoxy bonding, or even soldering or brazing. In this particular embodiment, the first end 206 is configured to be the proximal end, adjacent to a delivery device, however, in other embodiments, the filaments 204 may be held together at the second end 208 instead of the first end 206. In still other embodiments, the filaments 204 may be held together at both ends 206, 208. The shape memory metal of the filaments of the permeable shell 202 may be heat set in the globular configuration of the relaxed expanded state. Suitable superelastic shape memory metals may include alloys such as NiTi alloy and the like. The superelastic properties of such alloys may be useful in providing the resilient properties to the elongate filaments 204 so that they can be heat set in the form shown, fully constrained for delivery within an inner lumen of a microcatheter 61 and then released to self-expand back to substantially the original heat set shape of the globular configuration upon deployment within a patient's body. Further embodiments for devices and methods for heat setting permeable shells are described in co-owned U.S. Patent Application Publication No. 2009/0275974, published Nov. 5, 2009, and titled "Filamentary Devices for Treatment of Vascular Defects," which is incorporated herein by reference in its entirety for all purposes.

The permeable shell 202 is heat set into a secondary shape 214 that comprises six lobes 212a-f (or ribs, ears, projections, protuberances) that are circumferentially arrayed with respect to the longitudinal axis 210 of the permeable shell 202. A braided wall 220 of the permeable shell 202 has different mechanical characteristics than a wall of a permeable shell having a simple cylindrical shape (e.g., circular cross-section). Instead of a single radius of curvature being heat formed into the braided wall around the entire circumference, the braided wall 220 of the permeable shell 202 comprising the secondary shape 214 has a more complex contouring, and contains multiple radii of curvature, which can be seen in more detail in FIGS. 7 and 8.

Figure 7:
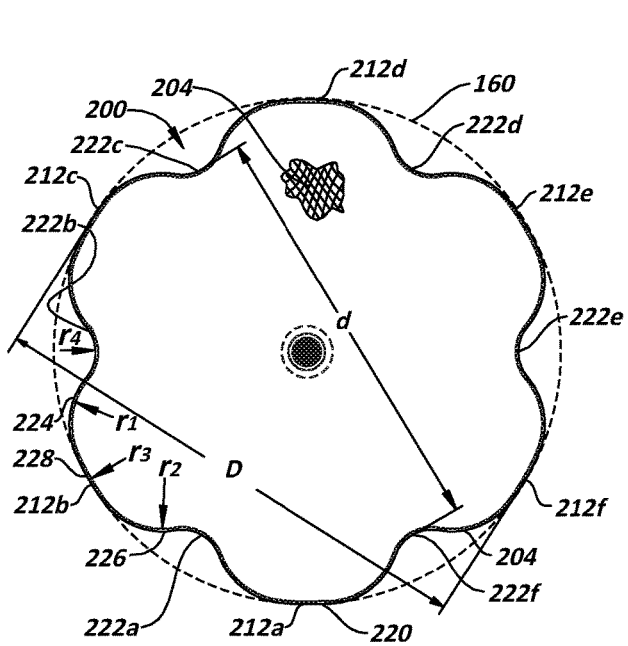
FIG. 7 is a first cross-sectional view of the device of FIG. 6 deployed within an aneurysm.
Figure 8:
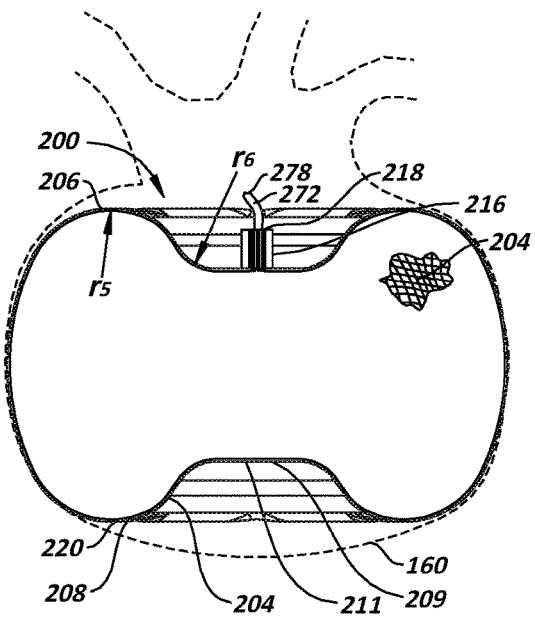
FIG. 8 is a second cross-sectional view of the device of FIG. 6 deployed within an aneurysm.

FIGS. 7 and 8 show cross-sectional views of the device for treatment of a vascular defect 200 deployed within a vascular defect 160, which in this particular case is an aneurysm. As shown in FIG. 7, the lobes 212a-f are evenly distributed around the longitudinal axis 210, and may be separated from each other by about 60°. In alternative embodiments, an uneven distribution may be desired, and may be achieved by using a different forming fixture during the heat setting operation. As shown in both FIGS. 6 and 7, between each of the lobes 212a-f is a longitudinally-extending channel 222a-f. The lobes 212a-f are shown in FIG. 6 extending substantially between the first end 206 and the second end 208 of the permeable shell 202. The channels 222a-f may extend substantially between the first end 206 and the second end 208 of the permeable shell 202. In other embodiments, distal ends of adjacent lobes may blend into one another and/or proximal ends of adjacent lobes may blend into one another such that the channels 222a-f do not extend completely between the first end 206 and the second end 208 of the permeable shell, 202, but instead are present only in a central portion of the permeable shell 202. The channels 222a-f may be configured to provide a fold or a pleat to allow the permeable shell 202 to selectively collapse into a desired constricted or compressed shape, for placement through the lumen 111 of a microcatheter 61.

As best seen in FIG. 7, each lobe 212a-f has a first side 224 having a first radius of curvature r1 and a second side 226 having a second radius of curvature r2. In the embodiment of FIG. 7, the first radius of curvature r1 is about equal to the second radius of curvature r2, but in other embodiments, they may differ. Each lobe 212a-f may also include a central section 228, between the first side 224 and the second side 226, the central section 228 having a third radius of curvature r3. In some embodiments, the third radius r3, is larger than the first radius of curvature r1 and larger than the second radius of curvature r2, and in other embodiments, the third radius r3 is smaller than the first radius of curvature r1 and smaller than the second radius of curvature r2. Each channel 222a-f may have a fourth radius of curvature r4. By heat setting the braided wall 220 into several smaller radii of curvature, for example, radii of curvature r1, r2, and r4, an expanded state of the permeable shell 202 may be produced that resists compression over time, for example, radial compression by repetitive blood pressure cycling when the device for treatment of a vascular defect 200 resides within a vascular defect 160 after implantation. The adjacent and opposing radii of curvature in the braided wall 220, for example, r1 and r4, create a bolstered structure that causes the lobe 212b (in this particular example) of the permeable shell 202 in its expanded state to resist compressive forces that would otherwise tend to crush, collapse or compress a single, larger-radiused portion of a purely circular braided wall, such as in a permeable shell having a circular cross-section of diameter D. The heat set smaller radii may increase the bending stiffness of the braided wall 220 in comparison to a purely circular cross-section braided wall having a diameter D. The permeable shell 202, in contrast, has a major diameter D and a minor diameter d. In some embodiments, a ratio (D/d) between the major diameter D and the minor diameter d is between about 1.05 and about 1.35, or between about 1.15 and about 1.25, or about 1.20. The generally wavy outer perimeter of the radial cross-section of the braided wall 220 shown in FIG. 7 may in some cases have larger dimension than a purely circular cross-section braided wall having a diameter D, for example, 0.5% to 10% larger.

In some embodiments, the major diameter D is between about two millimeters and about fourteen millimeters, or between about three millimeters and about twelve millimeters, or between about four millimeters and about eleven millimeters. In some embodiments, the length of the permeable shell 202 (e.g., measured along the longitudinal axis 210 between the first end 206 and second end 208) is between about two millimeters and about ten millimeters, or between about four millimeters and about eight millimeters.

In some embodiments, the third radius of curvature r3 is about equal to one-half the major diameter D of the permeable shell 202, thus the central sections 228 of the lobes 212a-f would each more or less follow the contours of a circle having a diameter D.

Returning to FIG. 6, a tether 272 is connected to the device for treatment of a vascular defect 200 at a first tether end 274. A second tether end 276 is configured to couple to a delivery or "pusher" device. In FIG. 8, the tether 272 has been cut, melted or otherwise severed during a detachment procedure, with only a small remnant 278 remaining. Also in FIG. 8, the second end 208 of the permeable shell 202 includes a closed end portion 209. Embodiments for devices and methods for producing devices for the treatment of vascular defects having closed end portions are described in U.S. Patent Application Publication No. 2016/02409934. The filaments 204 of the permeable shell 202 each have first ends 218a and second ends 218b which are secured at the first end 206 of the permeable shell 202. The filaments 204 also each have a central section 211 between the first end 218a and second end 218b which passes through or is incorporated into the closed end portion 209 of the second end 208 of the permeable shell 202.

In the longitudinal cross-section of the device for treatment of a vascular defect 200 in its expanded state in FIG. 8, other heat formed radii of curvature in the braided wall 220 serve to resist axial/longitudinal compression from factors such as repetitive blood pressure cycling. A fifth radius of curvature r5 is adjacent a generally opposed sixth radius of curvature r6. In some embodiments, the fifth radius of curvature r5 is larger than the sixth radius of curvature r6.

Representative ranges for the various radii of curvature, though non-limiting, are as follows. Radius of curvature r1 may range from about 0.29 millimeters to about 2.10 millimeters, or about 0.36 millimeters to about 1.10 millimeters. Radius of curvature r2 may range from about 0.29 millimeters to about 2.10 millimeters, or about 0.36 millimeters to about 1.10 millimeters. Radius of curvature r3 may range from about 0.29 millimeters to about 7.28 millimeters, or about 0.89 millimeters to about 2.69 millimeters. Radius of curvature r4 may range from about 0.16 millimeters to about 1.21 millimeters, or about 0.20 millimeters to about 0.63 millimeters. Radius of curvature r5 may range from about 0.28 millimeters to about 2.06 millimeters, or about 0.36 millimeters to about 1.09 millimeters. Radius of curvature r6 may range from about 0.16 millimeters to about 1.27 millimeters, or about 0.21 millimeters to about 0.65 millimeters.

Representative ranges for the ratios between different radii of curvature, though non-limiting, are as follows. The ratio r1/r3 may range from about 0.04 to about 2.49, or about 0.16 to about 0.48, or about 0.28 to about 0.36. The ratio r3/r4 may range from about 0.68 to about 44.18, or about 1.71 to about 6.42, or about 2.14 to about 6.31. The ratio r1/r4 may range from about 0.87 to about 12.39, or about 1.50 to about 2.61, or about 1.71 to about 1.77. The ratio r6/r5 may range from about 0.08 to about 4.08, or about 0.58 to about 0.90, or about 0.29 to about 0.63. The range of the ratio r2/r3 is expected to be similar to the range of the ratio r1/r3. The range of the ratio r2/r4 is expected to be similar to the range of the ratio r1/r4.

Though the device for treatment of a vascular defect 200 is depicted having six lobes 212a-f, other embodiments are possible which have a different number of lobes, for example, between two lobes and sixteen lobes, or even as many as thirty-two lobes or more.

Figure 9:
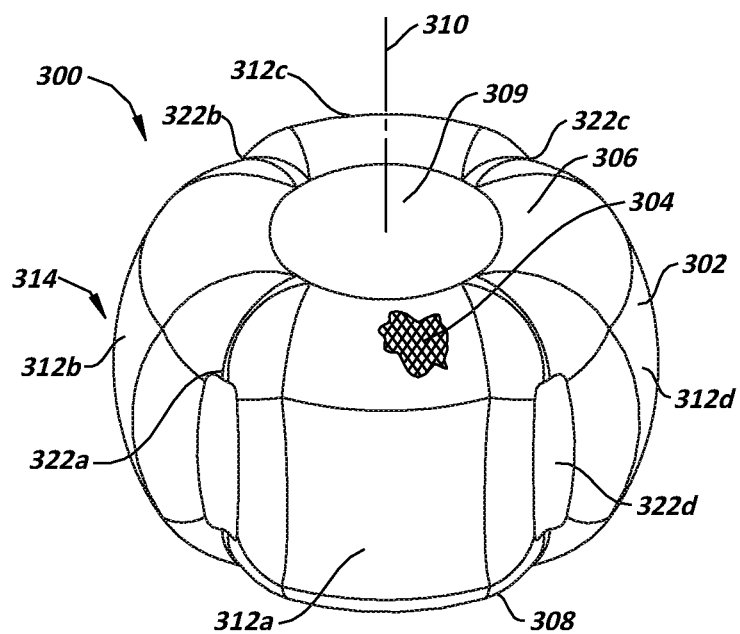
FIG. 9 is a perspective view of a device for treatment of vascular deformities according to an embodiment of the present disclosure.

FIG. 9 illustrates a device for treatment of a vascular defect 300 comprising a permeable shell 302 which is woven or braided from a plurality of resilient elongate filaments 304. The permeable shell 302 has a first end 306, a second end 308, and a longitudinal axis 310. Any of the materials and construction techniques described in relation to the device for treatment of a vascular defect 200 of FIG. 6, may also be used in constructing the device for treatment of a vascular defect 300. The permeable shell 302 is heat set into a secondary shape 314 that comprises four lobes 312a-d (or ribs, ears, projections, protuberances) that are circumferentially arrayed with respect to the longitudinal axis 310 of the permeable shell 302. Between each of the lobes 312a-d is a longitudinally-extending channel 322a-d. Also in FIG. 9, the first end 306 of the permeable shell 302 includes a closed end portion 309, which may be formed in the same manner as the closed end portion 209 of the device for treatment of a vascular defect 200 of FIG. 8.

Figure 10:
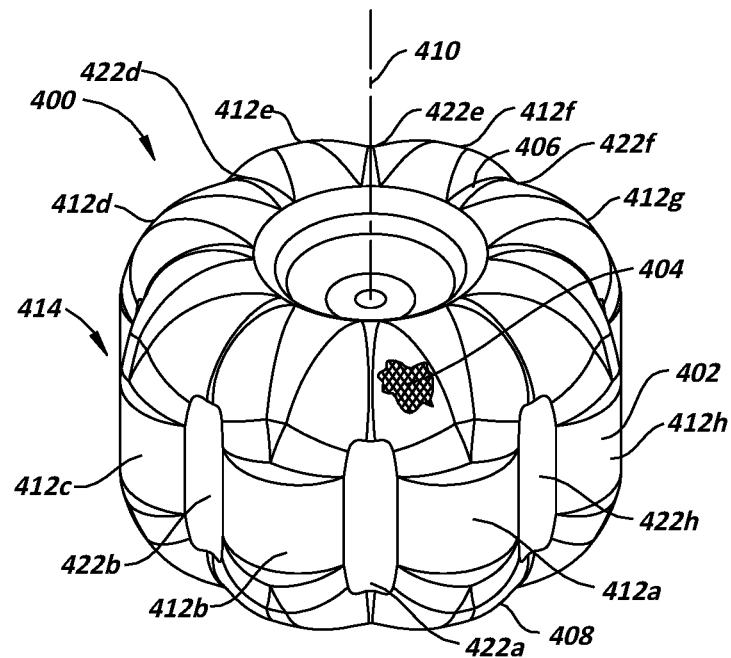
FIG. 10 is a perspective view of a device for treatment of vascular deformities according to an embodiment of the present disclosure.

FIG. 10 illustrates a device for treatment of a vascular defect 400 comprising a permeable shell 402 which is woven or braided from a plurality of resilient elongate filaments 404. The permeable shell 402 has a first end 406, a second end 408, and a longitudinal axis 410. Any of the materials and construction techniques described in relation to the device for treatment of a vascular defect 200 of FIG. 6 or the device for treatment of a vascular defect 300 of FIG. 9 may also be used in constructing the device for treatment of a vascular defect 400. The permeable shell 402 is heat set into a secondary shape 414 that comprises eight lobes 412a-h (or ribs, ears, projections, protuberances) that are circumferentially arrayed with respect to the longitudinal axis 410 of the permeable shell 402. Between each of the lobes 412a-h is a longitudinally-extending channel 422a-h. Each of the lobes 412a-h extends longitudinally with a generally semi-cylindrical shape arrayed around the outer periphery of the permeable shell 402. In this particular embodiment, each of the lobes 412a-h has an outer radius which is less than the one-half of the major diameter of the permeable shell 402.

It should be noted that the lobes 412a-h of the permeable shell 402 of FIG. 10, when cross-sectioned in a plane parallel to the longitudinal axis 410 in a midpoint along the longitudinal axis 410, do not have the multiple radii of curvature (e.g., where r1 is not equal to r3) that are displayed in the cross-section of the permeable shell 202 of FIG. 7. Instead a single radius of curvature (such that curvature r1, r2, and r3 are all equal to each other) exists between each adjacent and generally opposite radius of curvature r4. Thus, the eight lobes 412*a-h* each have a generally cylindrical outer contour at their outer extents.

Figure 11:
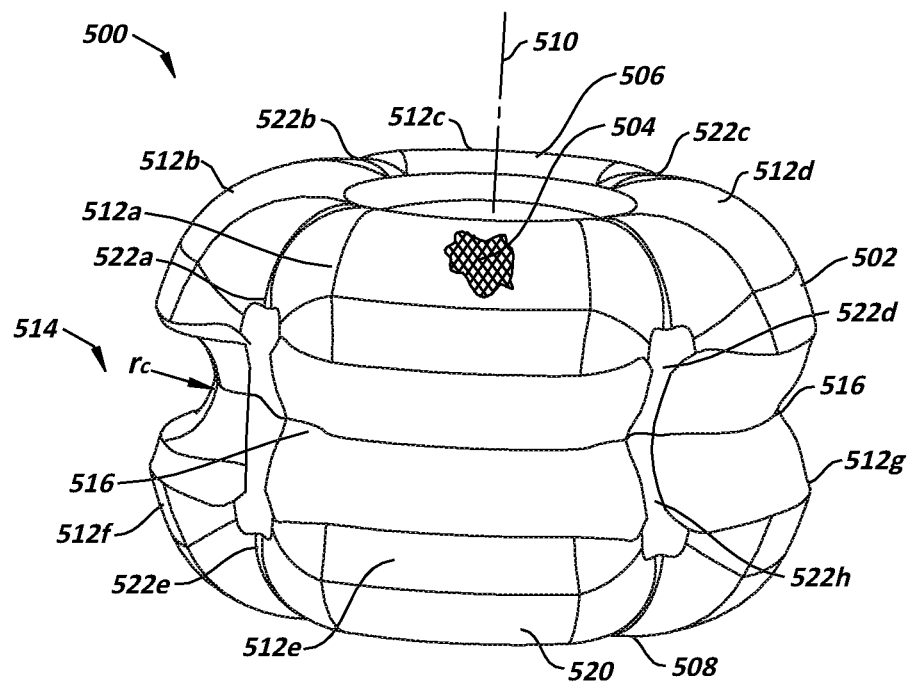
FIG. 11 is a perspective view of a device for treatment of vascular deformities according to an embodiment of the present disclosure.

FIG. 11 illustrates a device for treatment of a vascular defect 500 comprising a permeable shell 502 which is woven or braided from a plurality of resilient elongate filaments 504. The permeable shell 502 has a first end 506, a second end 508, and a longitudinal axis 510. Any of the materials and construction techniques described in relation to the device for treatment of a vascular defect 200 of FIG. 6, the device for treatment of a vascular defect 300 of FIG. 9, or the device for treatment of a vascular defect 400 of FIG. 10 may also be used in constructing the device for treatment of a vascular defect 500. The permeable shell 502 is heat set into a secondary shape 514 that comprises eight lobes 512*a-h* (or ribs, ears, projections, protuberances). Lobes 512*a-d* are circumferentially arrayed with respect to the longitudinal axis 510 of the permeable shell 502. Lobes 512*e-h* are also circumferentially arrayed with respect to the longitudinal axis 510 of the permeable shell 502. Between lobes 512*a-d* and lobes 512*e-h* is a circumferentially-extending channel 516 (groove, indentation, recess). The lobes 512*a-h* are also separated by longitudinally-extending channels 522*a-h*. The circumferentially-extending channel 516 may be heat formed in the braided wall 520 and has a cross-section having a semicircular shape with a radius of curvature rc. The radius of curvature rc serves to resist axial and even radial compression from factors such as repetitive blood pressure cycling, as described herein. In other embodiments, the cross-section of the circumferentially-extending channel 516 may have a substantially triangular shape. In other embodiments, the cross-section of the circumferentially-extending channel 516 may comprise two or more channels, each at a different longitudinal location along the longitudinal axis 510. For example, a first channel may be located closer to the first end 506 and a second channel may be located closer to the second end 508. Though the channel 516 is shown in FIG. 11 extending 360° around the longitudinal axis 510, in other embodiments, the channel may extend only partially around the longitudinal axis 510. In some embodiments, there may be two or more channels, each at about the same longitudinal location along the longitudinal axis 510, but each extending less than about 180° around the longitudinal axis. In one example, four different circumferentially-extending channels, each having comprising arc of about 80° are separated from each other by about 10°.

Figure 12:
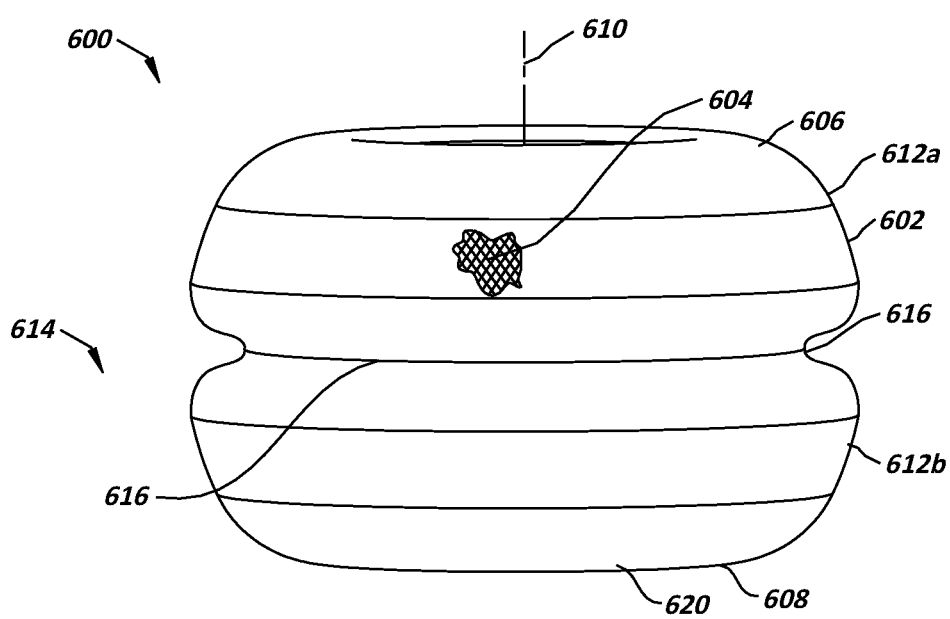
FIG. 12 is a perspective view of a device for treatment of vascular deformities according to an embodiment of the present disclosure.

FIG. 12 illustrates a device for treatment of a vascular defect 600 comprising a permeable shell 602 which is woven or braided from a plurality of resilient elongate filaments 604. The permeable shell 602 has a first end 606, a second end 608, and a longitudinal axis 610. Any of the materials and construction techniques described in relation to the device for treatment of a vascular defect 200 of FIG. 6, the device for treatment of a vascular defect 300 of FIG. 9, the device for treatment of a vascular defect 400 of FIG. 10, or the device for treatment of a vascular defect 500 of FIG. 11 may also be used in constructing the device for treatment of a vascular defect 600. The permeable shell 602 is heat set into a secondary shape 614 that comprises two lobes 612*a-b*. Between lobes 612*a* and 612*b* is a circumferentially-extending channel 616 (groove, indentation, recess). The circumferentially-extending channel 616 may be heat formed in the braided wall 620 and has a cross-section having a substantially triangular shape. The channel 616 serves to resist axial and even radial compression from factors such as repetitive blood pressure cycling, as described herein. In other embodiments, the cross-section of the circumferentially-extending channel 616 may have a semi-circular shape. In other embodiments, the cross-section of the circumferentially-extending channel 616 may comprise two or more channels.

In any of the embodiments described herein, the filaments 204, 304, 404 may include filaments of different transverse dimensions. For example, one sub-group of filaments may have an outer diameter of about 0.00075 inches and another sub-group of filaments may have an outer diameter of about 0.001 inches. There may even be three or more different sub-groups of filaments, each group having a particular transverse dimension and/or material composition. In some embodiments, one or more of the filaments may contain a radiopaque material such as platinum, platinum iridium, gold, or other materials, in order to increase the radiopacity of the permeable shell 202, 302, 402. In order to provide both superelastic and/or shape memory characteristics and radiopacity within each filament, a composite filament, such as a filament comprising a drawn filled tube (DFT) may be used. Some embodiments for composite and/or DFT filaments are described in U.S. Pat. No. 9,078,658.

Embodiments are contemplated which utilize filaments having transverse dimensions of between about 0.0005 inches and about 0.002 inches, or between about 0.00075 inches and about 0.00125 inches.

It can be appreciated that the multi-lobe geometry of the permeable shell 202, 302, 402 with a heat-formed secondary shape 214, 314, 414 having multiple radii or curvature resists in vivo compression of the permeable shell 202, 302, 402, both radial and axial/longitudinal compression, when the permeable shell 202, 302, 402 is in its expanded state or condition. However, some elongation of the permeable shell 202, 302, 402 occurs when the permeable shell 202, 302, 402 is being compressed into is compressed, radially constrained state or condition, and is aided by some sliding which is able to occur between the filaments 204, 304, 404. This makes the desired forced collapse on the permeable shell 202, 302, 402 for delivery through a catheter lumen simple and efficient, even though the device is able to resist compression while implanted in its expanded state over a significant length of time in a vascular defect.

While embodiments have been shown and described, various modifications may be made without departing from the scope of the inventive concepts disclosed herein. In additional to cerebral aneurysms, other types of aneurysms may be treated with devices described herein, including, but not limited to aortic aneurysms. Other vascular defects which may be treated with devices described herein include structural heart deformities, including, but not limited to left atrial appendages.

What is claimed is:

1. A device for treatment of a vascular defect within a patient's vasculature, comprising:
   a self-expanding permeable shell having a proximal end, a distal end, and a longitudinal axis, the shell comprising a plurality of elongate resilient filaments having a braided structure, wherein the filaments are secured at one or more of the proximal end or the distal end of the permeable shell, wherein the permeable shell has a radially constrained elongated state configured for delivery within a microcatheter and has an expanded state with an axially shortened configuration relative to the radially constrained state;
   the expanded shape of the permeable shell forming a plurality of extending lobes substantially between the proximal end and the distal end of the permeable shell, and a plurality of channels disposed between each of the plurality of lobes and extending substantially between the proximal end and the distal end of the permeable shell;

wherein each of the plurality of circumferentially-arrayed lobes comprises a first side having a first radius of curvature, a second side having a second radius of curvature and a central portion between the first side and the second side comprising a third radius of curvature;

wherein the third radius of curvature is greater than each of the first radius of curvature and the second radius of curvature.

2. The device of claim 1, wherein the plurality of lobes have a radial curvature that provides increased resistance to compressive force.

3. The device of claim 1, wherein the circumferentially-arrayed lobes are evenly distributed around the longitudinal axis of the permeable shell.

4. The device of claim 1, wherein the permeable shell comprises between two and sixteen circumferentially-arrayed lobes.

5. The device of claim 4, wherein the permeable shell is configured to pleat along each of the channels.

6. The device of claim 1, wherein the permeable shell in its expanded state has a major diameter D, and wherein each of the plurality of circumferentially-arrayed lobes has a radius of curvature r, wherein r<D/2.

7. The device of claim 6, wherein each of the plurality of elongate resilient filaments has a first end, a central section, and a second end, wherein the first and second ends of the plurality of filaments are secured at the proximal end of the permeable shell, and wherein the central section of each of the plurality of filaments passes through a distal region of the permeable shell.

8. The device of claim 1, wherein the permeable shell in its expanded state has a major diameter D which is between about two millimeters and about fourteen millimeters.

9. The device of claim 1, wherein the permeable shell has a major diameter D, and wherein the permeable shell has a minor diameter d, defined by the plurality of longitudinal channels, and wherein the ratio between the major diameter and the minor diameter is between about 1.05 and about 1.35.

10. The device of claim 1, wherein the permeable shell further comprises at least one recess extending circumferentially around at least a portion of a perimeter of the permeable shell perpendicularly relative to the longitudinal axis.

11. The device of claim 10, wherein the at least one recess comprises a continuous indented ring extending 360 degrees around the longitudinal axis.

12. The device of claim 11, wherein the at least one recess has a substantially semi-circular cross-section or a substantially triangular cross-section.

13. A device for treatment of a vascular defect within a patient's vasculature, comprising:

a shell comprising a braided mesh formed from a plurality of filaments and having a radially compressed configuration and a radially expanded configuration; the shell having a proximal end, a distal end, and a longitudinal axis extending through the proximal end and distal end;

wherein in the radially expanded configuration, the mesh forms a plurality of lobes that each are aligned with the longitudinal axis and that each curve outward from the longitudinal axis to increased resistance to bending;

wherein each of the plurality of circumferentially-arrayed lobes comprises a first side having a first radius of curvature, a second side having a second radius of curvature, and a central portion between the first side and the second side comprising a third radius of curvature; and wherein the third radius of curvature is greater than each of the first radius of curvature and the second radius of curvature.

14. The device of claim 13, further comprising a recess extending circumferentially and perpendicularly relative to the longitudinal axis.

15. A device for treatment of a vascular defect within a patient's vasculature, comprising:

a shell comprising a woven mesh formed from a plurality of filaments and having a radially compressed configuration and a radially expanded configuration; the shell having a proximal end, a distal end, and a longitudinal axis extending through the proximal end and distal end; the filaments being connected together at the proximal end; the proximal end having a detachment device that selectively detaches from a delivery device;

wherein in the radially expanded configuration, the mesh forms a plurality of lobes that each are aligned with the longitudinal axis and that each curve outward from the longitudinal axis to increased resistance to bending;

wherein each of the plurality of circumferentially-arrayed lobes comprises a first side having a first radius of curvature, a second side having a second radius of curvature, and a central portion between the first side and the second side comprising a third radius of curvature; and wherein the third radius of curvature is greater than each of the first radius of curvature and the second radius of curvature.

16. The device of claim 15, further comprising a recess extending circumferentially and perpendicularly relative to the longitudinal axis.

* * * * *